United States Patent [19]

Zilliken

[11] 4,234,577

[45] Nov. 18, 1980

[54] ERGOSTADIENTRIOLS, COMPOSITIONS CONTAINING SAME, AND METHODS OF PREPARING AND USING SAME

[75] Inventor: Fritz W. Zilliken, Remagen, Fed. Rep. of Germany

[73] Assignee: Z-L Limited Partnership, Janesville, Wis.

[21] Appl. No.: 22,202

[22] Filed: Mar. 19, 1979

Related U.S. Application Data

[63] Continuation-in-part of Ser. No. 804,594, Jun. 8, 1977, Pat. No. 4,157,984.

[51] Int. Cl.³ .................. A61K 31/56; A01N 45/00
[52] U.S. Cl. ........................... 424/238; 260/397.2; 424/240; 435/183
[58] Field of Search ............... /Steroids MS File; 424/238, 240, 241; 260/397.2

[56] References Cited

U.S. PATENT DOCUMENTS 4,102,884  7/1978  Kruger ........................ 260/397.2

OTHER PUBLICATIONS

"Steroids" by Fiesen et al., (1959), p. 98.

*Primary Examiner*—Elbert L. Roberts
*Attorney, Agent, or Firm*—Cooper, Dunham, Clark, Griffin & Moran

[57] ABSTRACT

The present invention concerns ergostadientriols which may be recovered from either the fungus *R. oligosporus* or the fungus *R. oryzae* as well as from soybeans which have been fermented with either of these fungi. Alternatively, the sterols may be chemically synthesized. The sterols of this invention are antioxidants which may be used in antioxidant compositions alone or preferably with one or more isoflavone. Of particular significance is the discovery that the ergostadientriols of this invention are useful in lowering serum cholesterol levels. Accordingly, this invention in a particularly preferred embodiment discloses pharmaceutical compositions containing one or more ergostadientriol. Finally, therapeutic methods which utilize pharmaceutical compositions in accordance with this invention are disclosed.

17 Claims, No Drawings

ERGOSTADIENTRIOLS, COMPOSITIONS CONTAINING SAME, AND METHODS OF PREPARING AND USING SAME

BACKGROUND OF THE INVENTION

This is a continuation-in-part of Application Ser. No. 804,594, filed June 8, 1977, now U.S. Pat. No. 4,157,984 the disclosure of which is hereby incorporated by reference into the present disclosure.

It has heretofore been known that antioxidant properties are possessed by tempeh, a fermented soybean product obtained by fermenting soybeans with a fungus, either *Rhizopus oligosporus* or *Rhizopus oryzae*. Food products containing tempeh, such as fish or fatty meat food products exhibit improved stability, see U.S. Pat. No. 3,681,085 (1972). Further, it has heretofore been found that by extracting tempeh with a mixture of hexane and ethanol, a component of tempeh, namely oil of tempeh, can be recovered, see U.S. Pat. Nos. 3,762,933 (1973) and 3,855,256 (1974), which exhibits enhanced antioxidant properties relative to those of tempeh. It has also been previously known that the average serum cholesterol levels of persons living in Indonesia where tempeh is a food staple are reduced relative to those of persons living in Western countries.

SUMMARY OF THE INVENTION

The present invention involves the discovery that ergostadientriols which possess antioxidant properties are produced by the fungi *Rhizopus oligosporus* and *Rhizopus oryzae* and may be recovered therefrom. Alternatively, these ergostadientriols may be chemically synthesized. The ergostadientriols of this invention have the structure:

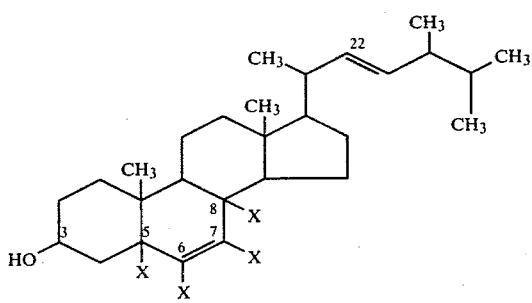

wherein X may be hydrogen or a hydroxyl group provided that X twice be hydroxyl. This structure is intended to cover both α and β stereoisomers of the substituents at the 5 and 7 positions and accordingly for the purposes of this application no distinction shall be made between the α and β isomers.

These compounds possess antioxidant properties and may be utilized in the stabilization of a wide variety of food products including edible fats and oils. Furthermore, antioxidant compositions which include one or more ergostadientriol in accordance with the present invention and one or more isoflavone have been found to be especially effective in stabilizing various food products.

A particularly significant aspect of the present invention involves the discovery that pharmaceutical compositions which include one or more ergostadientriol having the structure set forth hereinabove and a pharmaceutically acceptable carrier are useful in reducing serum cholesterol levels.

One or more of the ergostadientriols of the present invention may be prepared by culturing the fungus *R. oligosporus* or the fungus *R. oryzae* and recovering the compound or compounds therefrom. The fungus typically produces a mixture of ergostadientriols in the presence of ultraviolet light. Specific sterols can then be separately recovered. If the fungus is cultured in the present of visible light, the formation of one of the sterols is favored, specifically, the ergostadientriol having the structure:

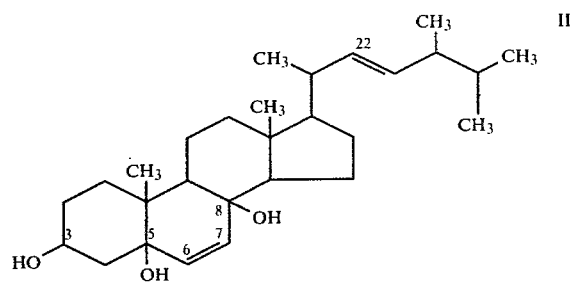

Compound II can then be isolated and recovered from the fungus. Additionally, one or more of the ergostadientriols can be prepared by fermenting soybeans with *R. oligosporus* or *R. oryzae*, contacting the resulting fermented soybean product, i.e. tempeh, with methanol to separate from the fermented soybean product an extract containing one or more of the ergostadientriols and recovering the compound or compounds from the methanol extract. As is the case where the ergostadientriols are prepared by culturing of one of the fungi identified hereinabove, the presence of visible light during fermentation of the soybeans results in preferential formation of ergostadientriol II. Alternatively, the ergostadientriols may be prepared by chemical synthesis.

Finally, the present invention provides methods of preventing and/or treating diseases involving increased serum cholesterol levels which involve administering an effective amount of a pharmaceutical composition such as described herein to a patient or subject having an abnormally high serum cholesterol level.

Thus, it is a primary object of the present invention to provide pharmaceutical compositions which include one or more ergostadientriol and a pharmaceutically acceptable carrier.

It is another object to provide a novel compound useful in pharmaceutical and/or antioxidant compositions.

It is a related object to provide methods of preparing such compounds.

It is still another object to provide methods of preventing and/or treating diseases which are associated with increased serum cholesterol levels. Such therapeutic methods involve administration of an effective amount of a pharmaceutical composition which includes one or more of the ergostadientriols of the present invention.

It is a final object of this invention to provide antioxidant compositions which include one or more of the ergostadientriols in accordance with this invention.

How these and other objects of this invention are accomplished will become apparent upon reading the detailed description of the invention including the examples set forth, and the claims which follow. In at least one embodiment of the present invention at least one of the foregoing objects will be achieved.

DETAILED DESCRIPTION OF THE INVENTION

In accordance with one embodiment of this invention, ergostadientriols having the structure:

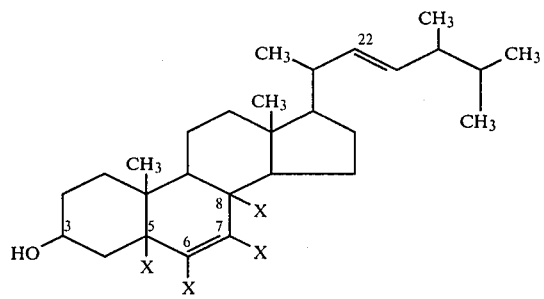

wherein X may be hydrogen or a hydroxyl group provided that X twice be hydroxyl have been prepared. These novel ergostadientriols possess antioxidative properties. They are "Emmerie Engel" positive at the same order of magnitude as Vitamin E, that is, they reduce $Fe^{+++}$ to $Fe^{++}$ at room temperature, the latter forming a brilliant red complex in the presence of α, α-dipyridil. In combination with various isoflavones, these sterols provide antioxidant compositions with exceptional properties. The ergostadientriols I have been characterized by ultraviolet, infrared, and high resolution mass spectrometry as 3-hydroxy-ergosterols. The molecular formula of these compounds is $C_{28}H_{46}O_3$, and their molecular weight 430. One such ergostadientriol has been identified as having the structure:

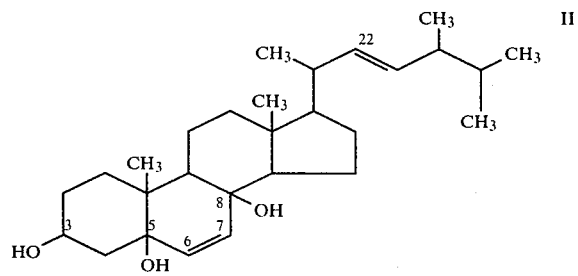

This ergostadientriol is a known compound, e.g., see Fisher and Fieser, *Steroids*, p. 98, (compound identified as Triol I(6)), Reinhold Publishing Corporation, New York (1959). However, its usefulness in reducing serum cholesterol levels has not previously been taught or suggested.

Another ergostadientriol has been identified as having the following structure:

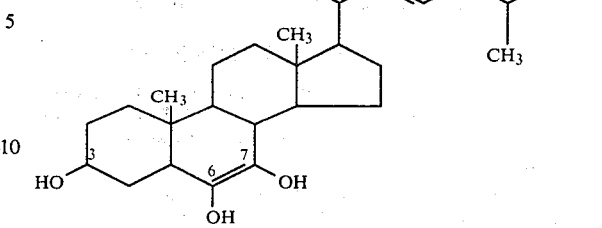

This ergostadientriol is a novel compound.

As indicated hereinabove, in a preferred embodiment, the present invention provides pharmaceutical compositions which are useful in reducing serum cholesterol levels. Such pharmaceutical compositions comprise one or more compound having the structure:

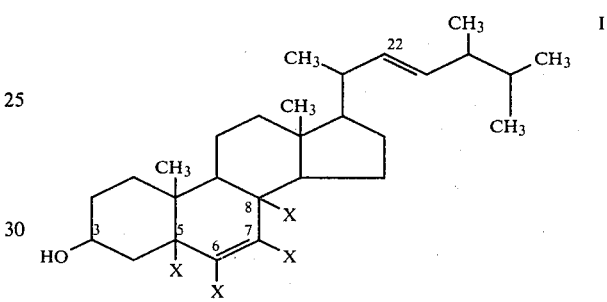

wherein X may be hydrogen or a hydroxyl group provided that X twice be hydroxyl, and a pharmaceutically acceptable carrier. Particularly preferred for use in such pharmaceutical compositions in ergostadientriol II which has the hydroxyl groups at the 5 and 8 positions. As used herein, pharmaceutically acceptable carrier includes without limitation all of the conventional carriers. Merely by way of illustration the following are set forth, namely, talc, starch, lactose, tragacanth, and magnesium sterate. Countless others are useful in the practices of the present invention and the choice of any specific carrier is one well within the skill of a person in the art.

Such pharmaceutical compositions may include one or more of the ergostadientriols of the present invention in amounts by weight ranging from about 0.001 to 10 percent, preferably, about 0.01 to 1.0 percent based upon the weight of said compositions. By administering such compositions to a patient or subject in an effective amount, such as an amount in the range 0.01–10 mg per kg of the patient's or subject's weight, serum cholesterol levels can be reduced. Accordingly, the present invention provides methods of preventing and/or treating diseases associated with increased serum cholesterol levels, such as atherosclerosis, which comprises administering to a subject or patient an effective amount of a pharmaceutical composition in accordance with the present invention.

In accordance with another embodiment of this invention, antioxidant compositions may be prepared which include one or more of the ergostadientriols I. As is disclosed more fully in co-pending, co-assigned application Ser. No. 804,594, filed June 8, 1977 referred to hereinabove and incorporated by reference into the present disclosure, compositions containing one or more ergostadientriol and one or more isoflavone provide exceptionally effective antioxidative properties. Specifically, antioxidant compositions which include an ergostadientriol having the structure:

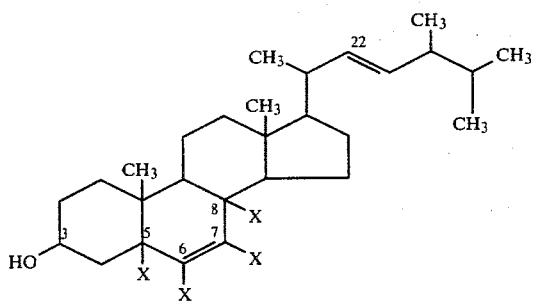

I wherein X may be hydrogen or a hydroxyl group provided that X twice be hydroxyl, and one or more isoflavone having the structure:

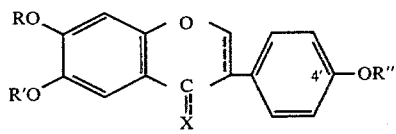

IV wherein the dashed lines may be carbon-carbon single bonds or carbon-carbon double bonds, and wherein X may be two hydrogen atoms or oxygen, and further wherein each of R, R' and R" may be a methyl group or hydrogen provide exceptional antioxidative properties as set forth in the examples hereinbelow.

Such antioxidant compositions can be included in food products to produce stabilized food compositions. Accordingly, food products such as fish, fatty meat or derivatives thereof, may be stabilized by the addition thereto of an antioxidant composition which includes one or more of the ergostadientriols described hereinabove in an amount from about 0.001 to 10 percent by weight. Additionally, stabilized edible oil and/or fat compositions may be prepared by including in edible oils or fats an antioxidant composition which includes one or more of the ergostadientriols of the present invention. Effective amounts of such antioxidant compositions in terms of improving the stability of oils or fats, such as for example, lard, corn oil, olive oil, soybean oil or palm oil, and the like are amounts in the range 0.01 to 1.0 percent by weight, more or less.

The ergostadientriols I may be produced by fermentation of soybeans with a fungus, either $R.$ $oligosporus$ or $R.$ $oryzae$. The ergostadientriols may also be produced by and recovered from either of these fungi directly after growth on a suitable culture medium. Suitable fungi for producing the ergostadientriols are $Rhizopus$ $oligosporus$ ATCC No. 22959 and $Rhizopus$ $oryzae$ ATCC No. 9363. If the fermentation of soybeans with fungus, or the culturing of fungus directly is carried out in the presence of ultraviolet light, a mixture of ergostadientriols, each of which falls within the scope of structure I is produced including compounds II and III. However, it has been found that if the fermentation or culturing is carried out in the presence of visible light, there is a preferential formation of ergostadientriol II which has the hydroxyl groups at the 5 and 8 positions as shown hereinabove. The ergostadientriol or ergostadientriols so prepared may be recovered in the following manner.

Dry, e.g., lyophilized, tempeh powder or cultured fungus is contacted with a 60–70% aqueous methanol solution for an extended period of time, for example, overnight, at a temperature of about 4° C. thereby producing an extract of methanol-soluble components including one or more of the ergostadientriols I. The methanol extract solution, after removal of insoluble material, is evaporated to dryness, preferably in vacuo, at an elevated temperature, for example, about 40°–60° C. A solid residue is produced, most of which is redissolved upon contact with dry methanol. That portion of the residue which is methanol insoluble is separated from the soluble components by centrifugation and discarded. After centrifugation the methanol supernatant is extracted with hexane several times, for example, two to three times, in order to remove any traces of hexane-soluble impurities, such as lipids. After discarding the resulting hexane extract, the remaining methanol supernatant is evaporated to reduce its volume to a minimal fraction, for example, about 20 ml, and kept at a temperature of about −20° C. for about 15–20 minutes. This results in formation of additional precipitate which is removed and discarded.

The ergostadientriols may then be recovered from the methanol supernatant or extract as follows. The supernatant is subjected to molecular sieve chromatography, for example, chromatography on Sephadex LH20 using a suitable size column, for example, 2×40 cm, and a suitable mobile phase, for example, n-propanol:ethylacetate:water in a ratio 5:5:1. One of the fractions resulting from this chromatographic separation is fluorescent with emission in the blue range of the visible spectrum. This blue fluorescent fraction is separated and subjected to adsorption chromatography on a suitable matrix, for example, silica gel, using an appropriate mobile phase, for example, ethylacetate:propanol:water=95:2:3. The resulting blue flurorescent fraction is then re-chromatographed on an adsorptive matrix, for example, silica gel again, employing a different mobile phase, for example, cyclohexane:dichloromethane:ethyl formate:formic acid=35:30:30:5. Each of the ergostadientriols present can then be recovered in essentially pure form using its differential mobility on the silica gel plate.

Additionally, the ergostadientriols may also be obtained in pure form from the methanol supernatant or extract by preparative high pressure liquid gas chromatography.

Alternatively, the ergostadientriols may be chemically synthesized. For example, ergostadientriol II may be prepared from ergosterol by the method outlined in Fieser and Fieser, $Steroids,$ p. 98 and referred to hereinabove.

In addition to the ergostadientriols discussed hereinabove it would appear that compounds having the structure

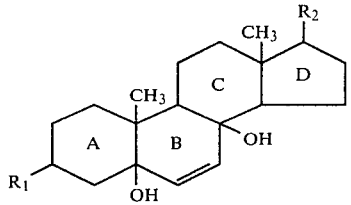

wherein $R_1$ may be —OH, =O, —H, —O—Alkyl, —O—Acyl, —COOH, —COOAlkyl or C≡N and wherein $R_2$ may be

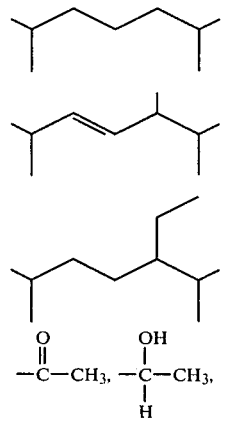

=O, or —H including without limitation the various sterochemically possible connections of Rings A,B,C and D, the reduction and addition reaction produces which may be obtained by reactions involving the double bond on $C_6$, particularly the epoxidation and hydroxylation products, and compounds having an additional double bond between $C_9$ and $C_{11}$ may be useful in lowering serum cholesterol levels.

EXAMPLE I

Ergostadientriol II was compared with β-sitosterol, a commercially available hypocholesterolemic agent to determine its effect upon serum cholesterol levels in chicks feed a high cholesterol diet.

In the bioassey there were four groups of three pens per group and five chicks per pen. Each group was fed a high cholesterol diet for seven days prior to blood sampling. One group served as control. Two groups were fed β-sitosterol at the level of 1.0% and 0.1% of the feed and one group was fed ergostadientriol II at a level of 0.1% of the feed. The results were as follows:

|  | Serum Cholesterol (mg %) |
| --- | --- |
| Control | 330.7 ± 15.8 |
| 0.1% β-sitosterol | 333.3 ± 7.9 |
| 1.0% β-sitosterol | 286.9 ± 14.9 |
| 0.1% ergostadientriol II | 283.8 ± 23.4 |

Statistical analysis of the data shows that the addition of 0.1% ergostadientriol II to the feed decreased serum cholesterol by 14.2% compared to the controls. 1.0% β-sitosterol was required to reduce cholesterol by 13.2% compared to the controls. Thus, ergostadientriol II was more than 10 times as active as β-sitosterol in reducing serum cholesterol.

The results of this test would indicate to one skilled in the art that the ergostadientriol would be effective in reducing serum cholesterol levels in human patients. Furthermore, these results would strongly suggest to one skilled in the art that the ergostadientriol would be useful in treating and/or preventing diseases associated with increased serum cholesterol levels such as athersclerosis.

EXAMPLE II

In a standard test assay involving oxidation of lard by exposure to air at 60° C. for 72 hours, ergostadientriol III may be added at a concentration of 0.1 percent by weight. This addition of the ergostadientriol should result in about 50% protection against oxidation.

EXAMPLE III

The same test as in Example II may be carried out except that the concentration of ergostadientriol III is 0.01 percent by weight. This reduced concentration should still provide about 25% protection against oxidation.

EXAMPLE IV

An antioxidant composition may be prepared by mixing ergostadientriol III and an isoflavone having the structure:

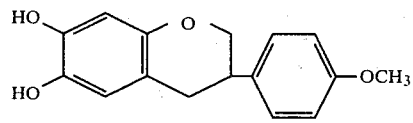

When added to lard at concentrations of each component of 0.01%, this composition should provide essentially 100% protection against oxidation in the standard assay.

EXAMPLE V

An antioxidant composition may be prepared by mixing ergostadientriol II and an isoflavone having the structure

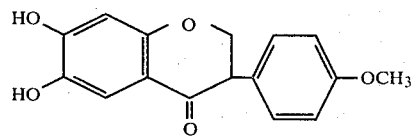

At a concentration of 0.01–0.1% by weight of each compound this antioxidant composition would provide substantial protection against oxidation.

As will be obvious to one skilled in the art, many modifications, variations, alterations and the like may be made in the practices of this invention without departing from the spirit and scope thereof as set forth in the claims which follow.

What is claimed is:

1. A composition useful as an antioxidant which comprises an effective antioxidative amount of a compound having the structure:

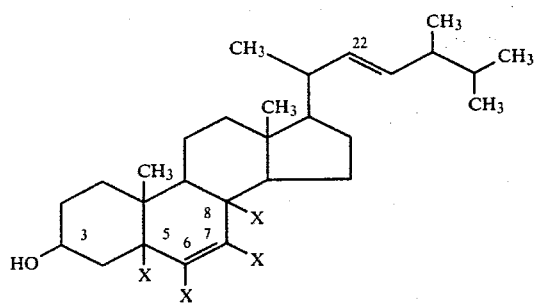

wherein X may be hydrogen or a hydroxyl group provided that X twice be hydroxyl and a carrier selected from the group consisting of edible foods, fats and oils.

2. A composition in accordance with claim 1 which comprises the compound having the structure:

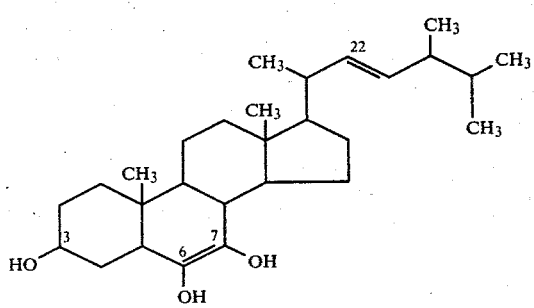

3. A composition in accordance with claim 1 which comprises a compound having the structure:

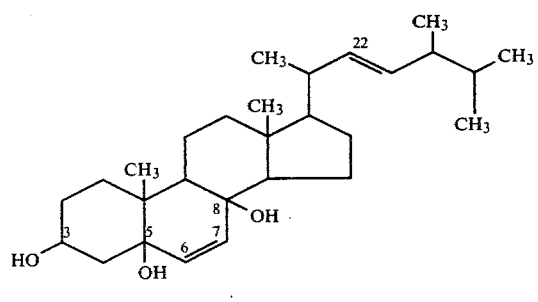

4. A composition in accordance with claim 1 which additionally comprises one or more isoflavone having the structure:

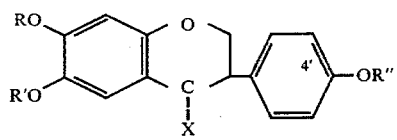

wherein the dashed lines may be carbon-carbon single bonds or carbon-carbon double bonds, and wherein X may be two hydrogen atoms or oxygen, and further wherein each of R, R' and R'' may be a methyl group or hydrogen.

5. A pharmaceutical composition useful in reducing serum cholesterol levels which comprises an effective hypocholesterolemic amount of a compound having the structure:

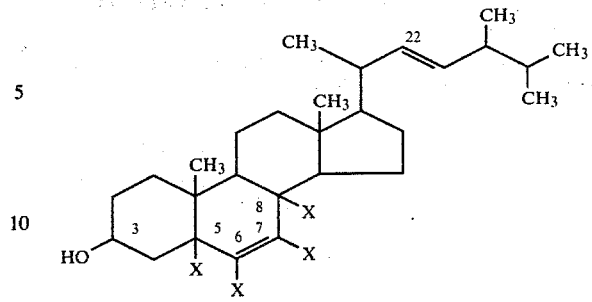

wherein X may be hydrogen or a hydroxyl group provided that X twice be hydroxyl and a conventional pharmaceutically acceptable carrier.

6. A pharmaceutical composition in accordance with claim 5 which comprises the compound having the structure:

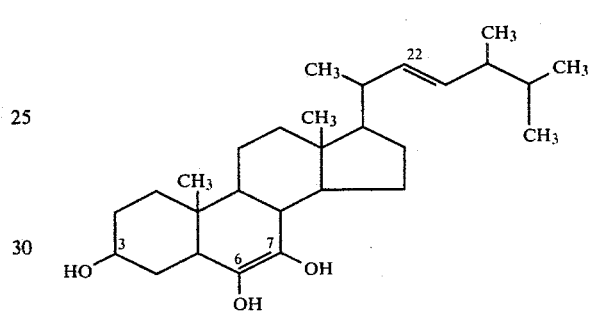

7. A pharmaceutical composition in accordance with claim 5 which comprises the compound having the structure:

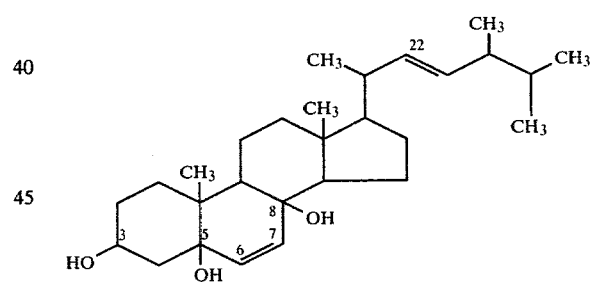

8. A method of preventing and/or treating diseases involving increased serum cholesterol levels which comprises administering to a subject an effective amount of a pharmaceutical composition in accordance with claim 5.

9. A method of preventing and/or treating diseases involving increased serum cholesterol levels which comprises administering to a subject an effective amount of a pharmaceutical composition in accordance with claim 6.

10. A method of preventing and/or treating diseases involving increased serum cholesterol levels which comprises administering to a subject an effective amount of a pharmaceutical composition in accordance with claim 7.

11. A method in accordance with claim 8 wherein said disease to be treated is atherosclerosis.

12. A method in accordance with claim 8 wherein said effective amount of pharmaceutical composition is an amount in the range 0.01–10 mg per kg of the subject's weight.

13. A compound having the structure:

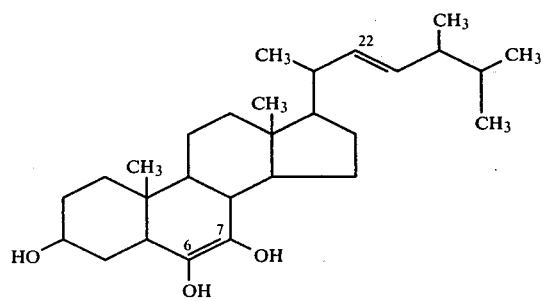

14. A pharmaceutical composition useful in reducing serum cholesterol levels which comprises an effective hypocholesterolemic amount of a compound having the structure:

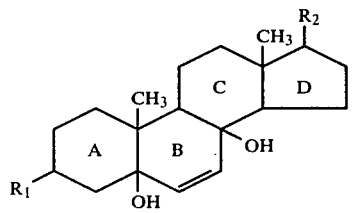

wherein $R_1$ may be —OH, =O, —H, —O—Alkyl, —O—Acyl, —COOH, —COOAlkyl or C≡N and wherein $R_2$ may be

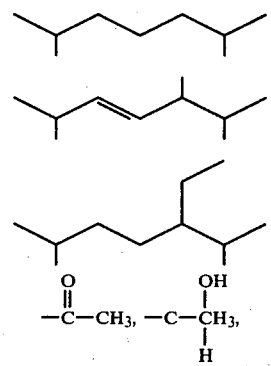

=O, or —H and a pharmaceutically acceptable carrier.

15. A method of preventing and/or treating diseases involving increased serum cholesterol levels which comprises administering to a subject an effective amount of a pharmaceutical composition in accordance with claim 14.

16. A method in accordance with claim 15 wherein said effective amount of pharmaceutical composition is an amount in the range 0.01–10 mg per kg of the subject's weight.

17. A method of preventing and/or treating hypercholesterolemia which comprises administering to a subject an effective amount of a pharmaceutical composition in accordance with any of claims 5, 6, 7 or 14.

* * * * *